United States Patent [19]

Renga et al.

[11] Patent Number: 5,324,837

[45] Date of Patent: Jun. 28, 1994

[54] 3,4-DISUBSTITUTED-4,5-DIHYDRO-1H-PYRAZOLES AND A METHOD OF PREPARATION

[75] Inventors: James M. Renga, Indianapolis, Ind.; Kevin L. McLaren, Concord, Calif.; James T. Pechacek, Clayton, Calif.; Michael J. Ricks, Concord, Calif.; Yulan C. Tong, Walnut Creek, Calif.

[73] Assignee: DowElanco, Indianapolis, Ind.

[21] Appl. No.: 931,791

[22] Filed: Aug. 17, 1992

Related U.S. Application Data

[63] Continuation-in-part of Ser. No. 842,834, Feb. 27, 1992, which is a continuation-in-part of Ser. No. 684,525, Apr. 11, 1991.

[51] Int. Cl.$^5$ ............... C07D 401/04; C07D 403/04; C07D 413/04; C07D 417/04
[52] U.S. Cl. ......................... 544/333; 544/238; 544/371; 544/315; 544/319; 544/316; 544/318; 544/326; 544/328; 544/327; 544/331; 546/167; 546/152; 546/153; 546/156; 546/279; 548/364.1; 548/127; 548/128; 548/129; 548/131; 548/132; 548/133; 548/134; 548/135; 548/137; 548/143; 548/144; 548/182; 548/186; 548/187; 548/189; 548/190; 548/193; 548/194; 548/195; 548/198; 548/200; 548/201; 548/202; 548/203; 548/204; 548/205; 548/206; 548/213; 548/214; 548/225; 548/228; 548/229; 548/233; 548/235; 548/236; 548/240; 548/243; 548/245; 548/246; 548/247; 548/248
[58] Field of Search ............... 546/167, 152, 153; 544/238, 315, 318, 327; 548/364.1, 127, 131, 134, 143, 186, 190, 195, 201, 204, 213, 228, 235, 243, 247

[56] References Cited

U.S. PATENT DOCUMENTS

| | | | |
|---|---|---|---|
| 3,991,073 | 11/1976 | Mulder et al. | 260/310 |
| 4,070,365 | 1/1978 | vanDaalen et al. | 548/379 |
| 4,174,393 | 11/1979 | vanDaalen et al. | 424/250 |
| 4,250,185 | 2/1981 | Gaughan | 424/273 |
| 4,839,376 | 6/1989 | Yamashita et al. | 514/406 |
| 4,863,947 | 9/1989 | Jacobson | 514/403 |
| 4,888,340 | 12/1989 | Neh et al. | 514/403 |
| 4,960,784 | 10/1990 | Lahm | 514/403 |
| 5,070,098 | 12/1991 | Fuchs et al. | 514/359 |
| 5,086,183 | 2/1991 | Fuchs et al. | 548/110 |

FOREIGN PATENT DOCUMENTS 466408 1/1992 European Pat. Off.

OTHER PUBLICATIONS

Weber et al, Zeitschrift for chemie, vol. 12(4) pp. 132-133 (1972).

Primary Examiner—John M. Ford
Attorney, Agent, or Firm—D. Wendell Osborne

[57] ABSTRACT 3,4-Diaryl-4,5-dihydro-1H-pyrazole compounds having a selected 5- or 6-membered aromatic heterocyclic moiety in the 4-position and an optionally substituted phenyl moiety in the 3-position, such as 4,5-dihydro-3-(4-fluorophenyl)-4-(5-trifluoromethyl-2-pyridinyl)-1H-pyrazole were prepared as intermediates in the preparation of insecticidal 3,4,N-triaryl-4,5-dihydro-1H-pyrazole-1-carboxamide compounds. The 3,4-diaryl-4,5-dihydro-1H-pyrazole compounds can be prepared from appropriate 1,2-diarylethanone compounds by successive treatments with N,N,N',N'-tetramethyl-diaminomethane in dichloromethane in the presence of acetic anhydride (to form a Mannich adduct) and hydrazine in the presence of a catalytic amount of trifluoroacetic acid.

27 Claims, No Drawings

3,4-DISUBSTITUTED-4,5-DIHYDRO-1H-PYRAZOLES AND A METHOD OF PREPARATION

CROSS-REFERENCE TO RELATED APPLICATIONS

This application is a continuation-in-part of copending application Ser. No. 07/842,834, filed Feb. 27, 1992, which is a continuation-in-part of copending application Ser. No. 07/684,525, filed Apr. 11, 1991, both of which applications are hereby incorporated by reference.

BACKGROUND OF THE INVENTION

The present invention relates to 3,4-di-substituted-4,5-dihydro-1H-pyrazole compounds that are intermediates to 3,4,N-trisubstituted-4,5-dihydro-1H-pyrazole-1-carboxamide compounds wherein the substituent in the 4-position is an optionally substituted 5- or 6-membered aromatic heterocyclic moiety and the substituents in the 3-position and the N-position are optionally substituted phenyl or optionally substituted 5- or 6-membered aromatic heterocyclic moleties.

A number of 3,4,N-trisubstituted-4,5-dihydro-1H-pyrazole-1-carboxamide compounds wherein all of the substituents are optionally substituted phenyl moieties have been prepared and found to possess insecticidal activity (U.S. Pat. Nos. 4,888,340, 4,174,393, and 4,070,365). Certain 3,5,N-trisubstituted-4,5-dihydro-1H-pyrazole-1-carboxamide compounds possessing unsubstituted pyridinyl as well as phenyl substituent moleties in the 3- and 5-positions and their insecticidal utility have also been disclosed (U.S. Pat. No. 3,991,073). Certain N-aryl-3-phenyl-4-aryl-4-(alkyl or alkoxycarbonyl)-4,5-dihydro-1H-pyrazole-1-carboxamide compounds are disclosed generically in U.S. Pat. No. 4,863,947 and an example wherein the 4-aryl moiety is 2-benzoxazolyl and the other 4-substituent is methyl is described. Some 3,4-disubstituted-4,5-dihydro-1H-pyrazole compounds that are required intermediates for these compounds are described in the same documents. A process for the preparation of certain 3,4-disubstituted-4,5-dihydro-1H-pyrazole compounds is given in U.S. Pat. No. 4,250,185.

SUMMARY OF THE INVENTION 3,4,N-Trisubstituted-4,5-dihydro-1H-pyrazole-1-carboxamide compounds

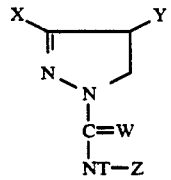

wherein the substituent in the 4-position (Y) is an optionally substituted pyridinyl, quinolinyl, pyrimidinyl, pyrazinyl, pyridazinyl, oxazolyl, isoxazolyl, thiazolyl, isothiazolyl, oxadiazolyl, or thiadiazolyl moiety, the substituent in the 3-position (X) is an optionally substituted phenyl moiety, the substituent in the N-position (Z) is an optionally substituted phenyl moiety, W is oxygen or sulfur, and T is hydrogen or an easily removed moiety, have been found to possess surprisingly good insecticidal utility.

In order to prepare the insecticidal compounds noted, appropriate 3,4-disubstituted-4,5-dihydro-1H-pyrazole compounds are required. These required 3,4-disubstituted-4,5-dihydro-1H-pyrazole compounds include the compounds of Formula I:

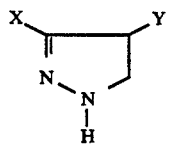

Formula I wherein
Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety wherein said substituents are selected from F, Cl, Br, CN, COQ, CF$_3$, OR', SR', NO$_2$, and OAr or a 5-membered aromatic heterocyclic ring moiety containing one ring oxygen or sulfur atom and one or two ring nitrogen atoms optionally substituted with one substituent selected from F, Cl, Br, CN, COQ, R, OR', SR', SOR', SO$_2$R', NO$_2$, and OAr and, in those moieties containing only one ring nitrogen atom, optionally additionally substituted with a F substituent;
X represents phenyl optionally substituted in the 4-position with F, Cl, Br, CN, COQ, R, OR', SR', SOR', SO$_2$R', NO$_2$, or OAr and/or in the 3-position with F, Cl, Br, CN, R, or OR';
Q represents OR'', SR'', NH$_2$, NHR'', or NR''$_2$;
R represents C$_1$–C$_3$ alkyl, C$_2$–C$_3$ alkenyl, or C$_2$–C$_3$ alkynyl optionally singly to completely substituted with fluorine or chlorine;
R' represents C$_1$–C$_3$ alkyl optionally singly to completely substituted with fluorine or chlorine;
R'' represents C$_1$–C$_4$ alkyl, C$_3$–C$_4$ alkenyl, or C$_3$–C$_4$ alkynyl; and
Ar represents phenyl optionally substituted with 1 or 2 compatible substituents selected from F, Cl, Br, CN, COQ, R, OR', SR', SOR', SO$_2$R', and NO$_2$.

3,4-Disubstituted-4,5-dihydro-1H-pyrazole compounds of Formula I wherein Y represents a 5-substituted-2-pyridinyl, 6-substituted-3-pyridinyl, 5-substituted-2-pyrimidinyl or 2-substituted-5-pyrimidinyl moiety or a thiazolyl or oxazolyl moiety attached to the dihydropyrazole ring at one position adjacent to the oxygen or sulfur atom and possessing a substituent in the other position adjacent to the oxygen or sulfur atom and X represents an optionally substituted phenyl moiety are often preferred.

The invention includes a process for preparing the compounds of Formula I which comprises combining an ethanone compound of Formula IV:

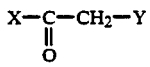

Formula IV wherein
Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety wherein said substituents are selected from F, Cl, Br, CN, COQ, CF$_3$, OR', SR', NO$_2$, and OAr or a 5-membered aromatic heterocyclic ring moiety containing one ring oxygen or sulfur atom and one or two ring nitrogen atoms optionally substituted with one substituent selected from F, Cl, Br, CN, COQ, R, OR', SR', SOR', SO$_2$R', NO$_2$, and OAr and, in those moieties containing only one ring nitrogen atom, optionally additionally substituted with a F substituent;

X represents phenyl optionally substituted in the 4-position with F, Cl, Br, CN, COQ, R, OR', SR', SOR', SO$_2$R', NO$_2$, or OAr and/or in the 3-position with F, Cl, Br, CN, R, or OR';

Q represents OR'', SR'', NH$_2$, NHR'', or NR''$_2$;

R represents C$_1$-C$_3$ alkyl, C$_2$-C$_3$ alkenyl, or C$_2$-C$_3$ alkynyl optionally singly to completely substituted with fluorine or chlorine;

R' represents C$_1$-C$_3$ alkyl optionally singly to completely substituted with fluorine or chlorine;

R'' represents C$_1$-C$_4$ alkyl, C$_3$-C$_4$ alkenyl, or C$_3$-C$_4$ alkynyl; and Ar represents phenyl optionally substituted with 1 or 2 compatible substituents selected from F, Cl, Br, CN, COQ, R, OR', SR', SOR', SO$_2$R', and NO$_2$ in an optionally chlorinated hydrocarbon solvent with an approximately equimolar amount of an N,N,N',N'-tetra-(C$_1$-C$_3$)alkyldiaminomethane, dipiperidinomethane, dipyrrolidinylmethane or N,N',N''-tri(C$_1$-C$_3$)alkylhexahydro-1,3,5-triazine compound and an approximately equimolar amount of an acid or anhydride of the formula

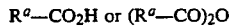

R$^a$—CO$_2$H or (R$^a$—CO)$_2$O wherein R$^a$ represents (C$_1$-C$_4$)alkyl or phenyl, each optionally monosubstituted to completely substituted with F or Cl, or H at about −10° C. to about 30° C. to obtain an intermediate Mannich adduct of the formula:

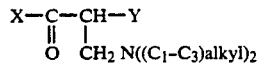

```
X—C—CH—Y
   ‖  |
   O  CH₂ N((C₁-C₃)alkyl)₂
``` wherein each of the substituents are defined as above, and, without isolation, adding hydrazine at about 0° C. to about 50° C., optionally in the presence of an added catalytic amount of a strong acid to obtain a compound of Formula I wherein each of the substituents is defined as above.

The compounds of Formula I prepared in the manner described can, with or without isolation, be treated with optionally substituted phenyl isocyanate or isothiocyanate compounds to obtain insecticidal 3,4,N-trisubstituted-4,5-dihydro-1H-pyrazole-1-carboxamide compounds.

DETAILED DESCRIPTION OF THE INVENTION

The compounds of the present invention are 3,4-diaryl-4,5-dihydro-1H-pyrazole compounds of Formula I wherein Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety wherein said substituents are selected from F, Cl, Br, CN, COQ, CF$_3$, OR', SR', NO$_2$, and OAr or a 5-membered aromatic heterocyclic ring moiety containing one ring oxygen or sulfur atom and one or two ring nitrogen atoms optionally substituted with one substituent selected from F, Cl, Br, CN, COQ, R, OR', SR', SOR', SO$_2$R', NO$_2$, and OAr and, in those moieties containing only one ring nitrogen atom, optionally additionally substituted with a F substituent and X represents phenyl optionally substituted in the 4-position with F, Cl, Br, CN, COQ, R, OR', SR', SOR', SO$_2$R', NO$_2$, or OAr and/or in the 3-position with F, Cl, Br, CN, R, or OR'. In these definitions Q represents OR'', SR'', NH$_2$, NHR'', or NR''$_2$; R represents C$_1$-C$_3$ alkyl, C$_2$-C$_3$ alkenyl, or C$_2$-C$_3$ alkynyl optionally singly to completely substituted with fluorine or chlorine; R' represents C$_1$-C$_3$ alkyl optionally singly to completely substituted with fluorine or chlorine; R'' represents C$_1$-C$_4$ alkyl, C$_3$-C$_4$ alkenyl, or C$_3$-C$_4$ alkynyl; and Ar represents phenyl optionally substituted with 1 or 2 compatible substituents selected from F, Cl, Br, CN, COQ, R, OR', SR', SOR', SO$_2$R', and NO$_2$.

4,5-Dihydro-1H-pyrazole compounds are sometimes informally referred to as 2-pyrazoline or Δ2-pyrazoline compounds.

The compounds of Formula I exist in two enantiomeric isomer forms because the 4-position ring carbon atom is asymmetrically substituted. The present invention relates to each of the enantiomeric isomers and to all mixtures of these isomers.

Compounds of Formula I wherein Y represents a 5-substituted-2-pyridinyl, 6-substituted-3-pyridinyl, 5-substituted-2-pyrimidinyl, or 2-substituted-5-pyrimidinyl moiety or a thiazolyl, or oxazolyl moiety attached to the dihydropyrazole ring at one position adjacent to the oxygen or sulfur atom and possessing a substituent in the other position adjacent to the oxygen or sulfur atom are generally preferred. Compounds wherein Y represents a 5-substituted-2-pyridinyl or a 5-substituted-2-pyrimidinyl moiety are sometimes more preferred. Compounds of Formula I wherein the substituents of the Y heterocycle are selected from F, Cl, Br, CN, CF$_3$, OCF$_2$H, and OCF$_3$ are generally preferred.

Compounds of Formula I wherein X represents substituted phenyl (as defined hereinabove) are usually preferred. Such compounds wherein the substituent is in the 4-position are generally more preferred and those wherein that substituent is selected from F, Cl, Br, CF$_3$, OCF$_2$H, OCF$_3$, OCH$_2$CF$_3$, OCF$_2$CF$_2$H, SO$_2$CF$_3$, and SCF$_3$ are usually most preferred. Compounds wherein X represents 4-fluorophenyl and 4-chlorophenyl are of particular interest.

Specifically preferred compounds of Formula I include 4,5-dihydro-3-(4-fluorophenyl)-4-(5-trifluoromethyl-2-pyridinyl)-1H-pyrazole, 4-(5-cyano-2-pyridinyl)-4,5-dihydro-3-(4-fluorophenyl)-1H-pyrazole, 4,5-dihydro-3-(4-fluorophenyl)-4-(5-fluoro-2-pyridinyl)-1H-pyrazole, 4-(5-chloro-2-pyridinyl)-4,5-dihydro-3-(4-fluorophenyl)-1H-pyrazole, 4-(5-chloro-2-pyrimidinyl)-4,5-dihydro-3-(4-fluorophenyl)-1H-pyrazole, 3-(4-chlorophenyl)-4-(5-chloro-2-pyridinyl)-4,5-dihydro-1H-pyrazole, 4-(5-chloro-2-pyrimidinyl)-4,5-dihydro-3-(4-fluorophenyl)-1H-pyrazole, 4,5-dihydro-3-(4-fluorophenyl)-4-(5-fluoro-2-pyrimidinyl)-1H-pyrazole, 4-(5-chloro-2-thiazolyl)-4,5-dihydro-3-(4-fluorophenyl)-1H-pyrazole, 4,5-dihydro-3-(4-fluorophenyl)-4-(2-trifluoromethyl-5-thiazolyl)-1H-pyrazole, 4,5-dihydro-3-(4-fluorophenyl )-4-(3-trifluoromethyl-5-isothiazolyl)-1H-pyrazole, 4,5-dihydro-3-(4-fluorophenyl)-4-(2-trifluoromethyl-5-oxazolyl)-1H-pyrazole, and 3-(4-chlorophenyl)-4,5-d ihydro-4-(2-trifluoromethyl-5-thiazolyl)-1H-pyrazole.

The compounds of Formula I are required intermediates for the insecticidal 3,4,N-trisubstituted-4,5-dihydro-1H-pyrazole-1-carboxamide compounds shown below wherein X and Y are as defined for compounds of Formula I and Z represents phenyl optionally substituted in the 4-position with F, Cl, Br, CN, COQ, R, OR', SR', SOR', SO₂R', OSO₂R', NO₂, or OAr and optionally in the 2-position with F and optionally in the 3- or 5-position with F, Cl, Br, CN, R, or OR'. Those such compounds wherein T represents H can be prepared by the reaction of an appropriate 3,4-disubstituted-4,5-dihydro-1H-pyrazole compound of Formula I with an appropriate isocyanate or isothiocyanate compound of Formula II as illustrated below. n

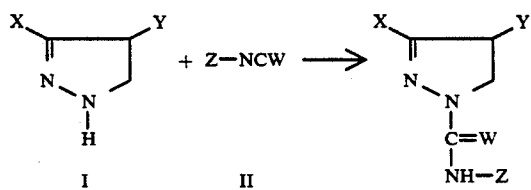

The reaction is generally effected by combining the 3,4-disubstituted-4,5-dihydro-1H-pyrazole compound and the isocyanate or isothiocyanate compound in the presence of an inert organic solvent, such as dichloromethane, 1,2-dichloroethane, chlorobenzene, toluene, acetonitrile, and the like, at a temperature of about 0° C. to about 60° C. and, typically, with agitation. The reaction takes place fairly rapidly, usually in about 0.1 to 20 hours. The 3,4,N-trisubstituted-4,5-dihydro1H-pyrazole-1-carboxamide and thiocarboxamide products are solids and can be recovered by conventional means, such as by filtration, centrifugation, or removal of the volatiles by evaporation. The initially recovered products can be further purified by conventional means, such as by recrystallization.

The 3,4-disubstituted-4,5-dihydropyrazole compounds of Formula I can be prepared by treatment of an appropriately substituted propenone compound of Formula III with hydrazine.

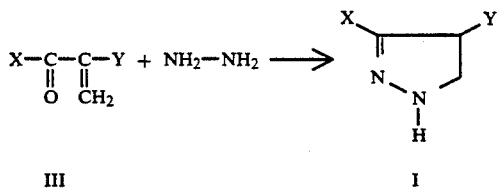

The reaction is typically effected by adding hydrazine, usually as the hydrate, to a solution of the propenone in a solvent, such as N,N-dimethylformamide or trifluoroacetic acid, at temperatures of about −20° C. to about 60° C. with agitation. After a reaction period of about 1 to about 8 hours the mixture is typically poured onto a mixture of ice and water with vigorous stirring. The desired product is typically recovered by extraction into an immiscible organic solvent, such as ether, and, if desired, further isolated by evaporation of the solvent. In those cases where the desired product precipitates as a solid, it can be recovered by filtration.

Compounds of Formula I are often unstable and degrade on attempted reerystallization or distillation. Accordingly, the crude products obtained are generally not recovered in pure form before being employed as intermediates. It is often preferred to remove water-soluble impurities by extracting a solution in a water-immiscible organic solvent with water or an aqueous solution and subsequently drying the solution. The compound of Formula I can be utilized in the form of the purified solution obtained. This type of procedure, when referring to compounds of Formula I, is designated herein as "without isolation".

The propenone compounds of Formula III can be prepared by the reaction of N,N,N',N'-tetramethylaminomethane and acetic anhydride with the appropriately substituted ethanone compound of Formula IV.

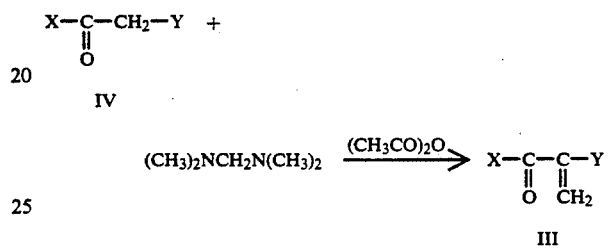

The reaction is generally carried out by adding excess acetic anhydride to a mixture of the ethanone compound of Formula IV in excess N,N,N',N'-tetramethylaminomethane at about 0° C. with agitation. The desired propenone compound of Formula III can be recovered by conventional means, such as by adding water and ether, separating the phases, and evaporating the volatile materials from the ethereal phase.

Alternately and preferably, the 3,4-disubstituted-4,5-dihydro-1H-pyrazole compounds of Formula I can be prepared from 1,2-disubstituted ethanone compounds of Formula IV in a one-pot process involving an intermediate Mannich adduct. The process can be carried out by combining an appropriate ethanone compound in an optionally chlorinated hydrocarbon solvent with an approximately equimolar amount of an N,N,N',N'-tetra(C₁-C₃)alkyldiaminomethane, N,N',N''-tri-(C₁-C₃)alkylhexahydro-1,3,5-triazine, dipiperidinomethane, or dipyrrolidinylmethane compound and an approximately equimolar amount of an acid or anhydride of the formula

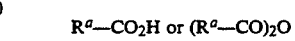

wherein R$^a$ represents (C₁-C₄)alkyl or phenyl, each optionally monosubstituted to completely substituted with F or Cl, or H at about −10° C. to about 30° C. to obtain an intermediate Mannich adduct of the formula:

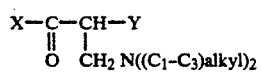

wherein X and Y are defined as compounds of Formula I, and, without isolation, adding hydrazine at about 0° C. to about 50° C., optionally in the presence of an added catalytic amount of a strong acid, to obtain a compound of Formula I wherein each of the substituents are defined as hereinbefore. Higher yields of compounds of Formula I are obtained in this simplified and less expensive process.

In the first step of the above process the optionally chlorinated hydrocarbon solvent is, for example, dichloromethane, chloroform, trichloroethylene, or 1,1,1-trichloroethane. One and two carbon chlorinated solvents, such as dichloromethane and chloroform, are typically preferred. The alkyl groups of the N,N,N',N'-tetra($C_1$-$C_3$)alkyldiaminomethane and N,N',N''-tri($C_1$-$C_3$)alkylhexahydro-1,3,5-triazine compounds may be methyl, ethyl, propyl, or methylethyl alkyl groups. Methyl is preferred and N,N,N',N'-tetramethyldiaminomethane is especially preferred. Suitable acids and anhydrides include formic, acetic, propionic, trifluoroacetic, benzoic, dichloroacetic, and the like. Acetic anhydride or trifluoroacetic acid are sometimes preferred. The term "approximately equimolar" includes at least molar ratios between about 1.25:1 and about 0.75:1. Mole ratios of about 1.1:1 to about 0.9:1 are more typical. The best results are often obtained at temperatures of about 0° C. to about 30° C. The reaction mixture is typically agitated.

In the second step of the above process the optionally added catalytic strong acid can be any acid having a kPa of about 2 or less that is readily soluble in the medium. Suitable strong acids include trifluoroacetic acid, dichloroacetic acid, methane-sulfonic acid, and the like. Trifluoroacetic acid is often preferred. A catalytic amount is typically between about 1 and about 50 mole percent of the starting material ethanone. The hydrazine can be anhydrous, the monohydrate, or an aqueous solution. It can, further, be prepared in situ from a mineral acid salt. Anhydrous hydrazine is usually preferred. The best results are often obtained at temperatures of about 10° C. to about 40° C. The reaction mixture is typically agitated.

The compounds of Formula I prepared in the above manner can, with or without isolation, be treated with an optionally substituted phenyl isocyanate or isothiocyanate compound to obtain insecticidal 3,4,N-triaryl-4,5-dihydro-1H-pyrazole-1-carboxamide compounds. When the compounds of Formula I are not isolated, the crude product is typically diluted with an inert, water-immiscible solvent, such as ether or dichloromethane, and the resulting solution is extracted with water or an aqueous solution and dried.

Certain of the ethanone compounds of Formula IV can be obtained by the reaction of an acetyl compound of Formula V with a pyridine, quinoline, pyrimidine, pyridazine, pyrazine, oxazole, thiazole, isothiazole, thiadiazole, or oxazole compound of Formula VI wherein E represents a fluoro, chloro, methanesulfonyl, benzenesulfonyl or other easily displaced moiety and Y is as defined hereinbefore.

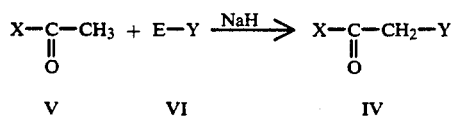

This method is especially valuable for the preparation of compounds of Formula IV wherein Y is a 2-pyridinyl, 2-pyrimidinyl, 2-pyrazinyl, 3-pyridazinyl, 2-quinolinyl, 2-thiazolyl, or 5-isothiazolyl moiety. The reaction can be carried out by adding a solution of the acetyl compound V to a slurry of sodium hydride in an inert solvent, such as tetrahydrofuran or toluene, with agitation. The resultant mixture is maintained at about 0° C. to 120° C., the compound of Formula VI is added, and the mixture is allowed to react. The mixture is then cooled, quenched with an acid, and the desired product recovered by conventional means.

Other of the ethanone compounds of Formula IV can be obtained by the reaction of a compound of Formula VII wherein X is defined as above and G represents an alkoxycarbonyl, N,N-dialkylaminocarbonyl, or cyano group with a methylpyridine, methylquinoline, methylpyridazine, methylpyrazine, methylpyrimidine, methylthiazole, methylisothiazole, methylthiadiazole, or methyloxadiazole compound of Formula VIII wherein Y is as defined above.

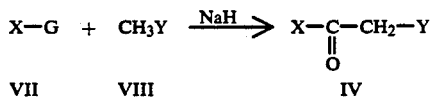

The reaction can be carried out by allowing the compound of Formula VIII to react with a strong base, such as butyl lithium, lithium dimethylamide, or sodium hydride in an inert solvent, such as tetrahydrofuran, adding the compound of Formula VII, and allowing the mixture to react. The resultant reaction mixture is quenched with an acid, such as hydrochloric acid, or an acidic salt, such as ammonium chloride, and the desired product is recovered by conventional means.

Still other compounds of Formula IV can be prepared by hydration of a corresponding substituted acetylene compound of Formula IX wherein X and Y are as defined above.

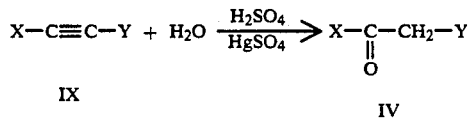

This method is especially valuable for preparing compounds of Formula IV wherein Y is a 3-pyridinyl, 3-quinolinyl, or 5-pyrimidinyl moiety. The reaction is generally carried out by heating at reflux for a few hours an aqueous mixture containing the compound of Formula IX, acetone, sulfuric acid, and mercuric sulfate and then recovering the ethanone compound by conventional means.

The acetylene compounds of Formula IX can be obtained by the reaction of a haloheterocycle, such as a halopyridine, halopyrimidine, halothiazole, or halooxazole compound of Formula X wherein Y is as defined above with an acetylene compound of Formula XI wherein X is as defined above.

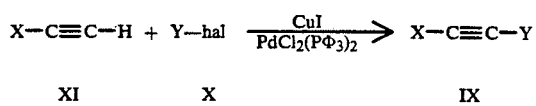

Bromine is usually the preferred halogen (hal) moiety. The reaction can be carried out by heating for about an hour a mixture of the compounds of Formula X and XI in the presence of catalytic amounts of cuprous iodide and the bistriphenylphosphine complex of palladium dichloride in a solvent composed typically of a mixture of triethylamine and N,N-dimethylformamide. The desired product can be recovered by conventional means.

Alternately, compounds of Formula IV can be prepared from a compound of Formula VIII and a benzaldehyde-trimethylsilyl cyanide adduct compound of Formula XIII. The methyl compound of Formula VIII is first brominated or chlorinated by a standard procedure and the bromomethyl or chloromethyl compound of Formula XII obtained is condensed with the compound of Formula XIII in the presence of a very strong base, such as lithium diisopropylamide. The resulting cyanohydrin is hydrolyzed by treatment with an aqueous acid and then an aqueous base to obtain the desired compound of Formula IV.

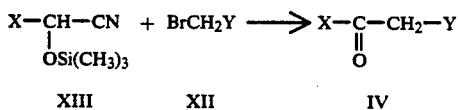

The compounds of Formulas V, VI, VII, VIII, XI, and XIII are well known in the art or can be prepared by procedures well known in the art. For example, 5-trifluoromethyl-2-chloropyrazine can be made from 5-chloropyrazine-2-carboxylic acid by successive treatments with a mixture of phosphorus pentachloride and phenylphosphonic dichloride and a mixture of hydrogen fluoride and antimony trichloride using conditions that are well known for similar conversions of pyridine-carboxylic acids.

EXPERIMENTAL

General. Reagents and solvents were used as purchased from commercial suppliers. All reactions involving organometallic reagents were conducted in a dry nitrogen atmosphere using oven-dried glassware. Melting points (pyrex capillary) were uncorrected. Proton nuclear magnetic resonance spectroscopy (1H NMR) was performed using a Varian XL200 or Brucker AM400 spectrometer in CDCl3 as solvent, unless otherwise noted. 1H NMR data are presented as: chemical shift in parts per million (ppm) downfield from tetramethylsilane (multiplicity, number of hydrogens, coupling constant(s) in Hertz (Hz)).

EXAMPLE 1

Preparation of
2-(5-(Trifluoromethyl)-2-Pyridinyl)-1-(4-Chlorophenyl)Ethanone

4′-Chloroacetophenone (16 milliliters (mL), 19 grams (g), 120 millimoles (mmol)) was added rapidly dropwise to a stirring 21° C. slurry of sodium hydride (17.1 g, 428 mmol; freed of mineral oil by a hexane wash) in tetrahydrofuran (THF) (280 mL). After 1 hour (hr), the mixture was heated at reflux for 1 hr, then cooled to 21° C. 2-Fluoro-5-(trifluoromethyl)pyridine was added rapidly dropwise to the stirring slurry causing a rapid color change to dark red. The solution was heated at reflux for 17 hr, at which time gas chromatography (GC) analysis showed complete conversion. The mixture was cooled to 0° C. and quenched by careful sequential addition of acetic acid (12 mL, 13 g, 210 mmol), water (125 mL), acetic acid (12 mL, 13 g, 210 mmol), and water (125 mL). The layers were treated separately due to the propensity of this material to form serious emulsions. The aqueous layer was extracted with ether (2×100 mL). The combined organic layer was extracted with water and brine, dried over magnesium sulfate, decolorized with activated charcoal, filtered, and evaporated to a wet brown solid residue. 1H NMR showed a 59:41 molar ratio of ketone to enol tautomer. The residue was triturated with hexane and applied to a porous plate to obtain a pale yellow solid. The hexane solvent was evaporated and the residue combined with the solid. The mixture was purified by flash chromatography, eluting with methylene chloride, to obtain 12.6 g (50 percent of theory) of the title compound as a yellow solid melting at 114°–116° C. Attempts to recrystallize the compound generally resulted in some decomposition.

Elemental Analysis for $C_{14}H_9ClF_3NO$: Calc.: C, 56.11; H, 3.03; N, 4.67 Found: C, 55.71; H, 3.01; N, 4.59.

The following were prepared similarly:

2-(6-Fluoro-2-pyridinyl)-1-(4-fluorophenyl)ethanone; a semi-solid (63 percent yield);

Elemental Analysis for $C_{13}H_9F_2NO$: Calc.: C, 66.95; H, 3.89; N, 6.01 Found: C, 67.11; H, 4.02; N, 6.09.

2-(5-(Trifluoromethyl)-2-pyridinyl)-1-(4-fluorophenyl)ethanone; a yellow powder melting at 82°–83° C. and decomposing on recrystallization (45 percent of theory); 1H NMR (ketone tautomer) δ4.53 (s, 2), 7.13 (dd, 2, J=8.5, 8.5), 7.44 (d, 1, J=8.0), 7.85 (m, 1), 8.08 (dd, 2, J=5.4, 8.9), 8.81 (m, 1); 1H NMR (enol tautomer) δ6.06 (s, 1), 7.09 (dd, 2, J=8.7, 8.7), 7.13 (d, 1, J=8.5), 7.79 (dd, 1, J=2.4, 7.9), 7.83 (dd, 2, J=5.4, 9.0), 8.57 (br s, 1), 14.97 (s, 1).

Elemental Analysis for $C_{14}H_9F_4NO$: Calc.: C, 59.37; H, 3.20; N, 4.95 Found: C, 59.72; H, 3.07; N, 4.82.

2-(6-Chloro-2-quinolinyl)-1-(4-chlorophenyl)ethanone; an orange solid melting at 194°–195° C. (50 percent yield);

Elemental Analysis for $C_{17}H_{11}Cl_2NO$: Calc.: C, 64.58; H, 3.51; N, 4.43 Found: C, 64.58; H, 3.46; N, 4.41.

2-(7-Chloro-2-quinolinyl)-1-(4-chlorophenyl)ethanone; an orange solid melting at 181°–182° C. (34 percent yield);

Elemental Analysis for $C_{17}H_{11}Cl_2NO$: Calc.: C, 64.58; H, 3.51; N, 4.43 Found: C, 64.74; H, 3.73; 4.65.

2-(3-Fluoro-5-(trifluoromethyl)-2-pyridinyl)-1-(4-fluorophenyl)ethanone; a yellow powder (88 percent yield).

2-(5-Cyano-2-pyridinyl)-1-(4-chlorophenyl)ethanone; tan needles melting at 169°–170° C. (80 percent yield);

Elemental Analysis for $C_{14}H_9ClN_2O$: Calc.: C, 65.51; H, 3.53; N, 10.91 Found: C, 64.92; H, 3.27; N, 10.66.

2-(6-Chloro-4-pyrimidinyl)-1-(4-fluorophenyl)ethanone; yellow crystals melting at 98° C. (26 percent yield);

Elemental Analysis for $C_{12}H_8ClFN_2O$: Calc.: C, 57.50; H, 3.22; N, 11.18 Found: C, 57.60; H, 2.96; N, 11.01.

2-(5-Chloro-2-pyridinyl)-1-(4-fluorophenyl)ethanone; yellow needles melting at 95°–96° C. (34 percent yield);

Elemental Analysis for $C_{13}H_9ClFNO$: Calc.: C, 62.54; H, 3.63; N, 5.61 Found: C, 62.72; H, 3.71; N, 5.63.

2-(5-Trifluoromethyl-2-pyrazinyl)-1-(4-fluorophenyl)ethanone; yellow solid melting at 97°–100° C. (76 percent yield);

Elemental Analysis for $C_{13}H_8F_4N_2O$: Calc.: C, 54.94; H, 2.84; N, 9.86 Found: C, 55.24; H, 2.75; N, 10.08.

2-(6-Chloro-2-pyrazinyl)-1-(4-fluorophenyl)ethanone; ivory plates melting at 88.5°–90° C. (82 percent yield);

Elemental Analysis for $C_{12}H_8ClFN_2O$: Calc.: C, 57.50; H, 3.22; N, 11.18 Found: C, 57.78; H, 3.45; N, 11.34.

EXAMPLE 2

Preparation of
1-(4-Chlorophenyl)-2-(6-Chloro-3-Pyridazinyl)-1-Ethanone

Potassium hydride (6.86 g of 35 percent in mineral oil, 60 mmol, washed 3 times with hexane to remove the mineral oil) and 100 mg of 18-crown-6 ether catalyst were placed in a flask under argon and 80 mL of tetrahydrofuran (THF) was added. 3-Chloro-6-methylpyridazine (2.57 g, 22 mmol) as a solution in 7 mL of THF was added dropwise with stirring at ambient temperature over a 50 min period. The resulting slurry was cooled to −40° C. and a solution of methyl 4-chlorobenzoate (3.75 g, 22 mmol) in 5 mL of THF was added with stirring and cooling over a 5 min period. The mixture was allowed to warm to ambient temperature and was stirred for 8 hr at which time all of the 3-chloro-6-methylpyridazine had been consumed as determined by TLC. The mixture was poured into 200 mL of saturated aqueous ammonium chloride solution and the phases were separated. The aqueous phase was extracted 3 times with 100 mL portions of methylene chloride and all of the organic phases were combined and filtered through a plug (5 cm × 15 cm) of silica gel. The silica gel was extracted with a 10:90 mixture of ether and methylene chloride until the eluent was nearly colorless and the eluent was combined with the filtrate and concentrated by evaporation under reduced pressure. The residue was triturated with hexane and the solids were recovered by filtration and dried to obtain the title compound in 41 percent yield as a gold colored solid. An analytical sample melting at 152.5°–153.5° C. was obtained by recrystallization from hexane/acetone.

Elemental Analysis for $C_{12}H_8Cl_2N_2O$: Calc.: C, 53.96; H, 3.02; N, 10.49 Found: C, 53.68; H, 3.03; N, 10.24.

EXAMPLE 3

Preparation of
1-(4-Fluorophenyl)-2-(5-Pyrimidinyl)Ethanone

A solution of 5-(4-(fluorophenyl)ethynyl)pyrimidine (2.90 g, 15 mmol) and mercuric sulfate (4.3 g, 15 mmol) in 100 mL of 70 percent aqueous acetone containing 10.4 g of 98 percent sulfuric acid was prepared and heated at reflux with stirring for 6 hr. The volatiles were then removed by evaporation under reduced pressure and the residue was made basic with aqueous ammonia and was then extracted with ether (2×100 mL) and 100 mL of methylene chloride. The combined organic extracts were extracted with brine (2×100 mL), dried over magnesium sulfate, filtered, and concentrated under reduced pressure to obtain 2.4 g of the title compound in crude form. This was column chromatographed, eluting with a 50:50 mixture of hexane and ethyl acetate, to obtain 1.56 g (49 percent of theory) of the title compound as fine white needles melting at 86° C.

IR absorptions at 1699, 1597, 1561, 1507, 1409, 1335, 1216, and 832 cm$^{-1}$;

1H NMR δ4.26 (s, 2), 7.15 (dd, 2), 8.0 (dd, 2), 8.61 (s, 2), 9.11 (s, 1);

Elemental Analysis for $C_{12}H_9FN_2O$: Calc.: C, 66.66; H, 4.20; N, 12.96 Found: C, 66.72; H, 4.22; N, 12.65.

The following were prepared similarly:

1-Phenyl-2-(7-chloro-3-quinolinyl)ethanone; white crystals melting at 160°–161° C. (62 percent yield);

Elemental Analysis for $C_{17}H_{12}ClNO$: Calc.: C, 72.47; H, 4.29; N, 4.97 Found: C, 72.57; H, 4.17; N, 4.80.

1-Phenyl-2-(6-chloro-3-quinolinyl)ethanone; white crystals melting at 113°–114° C. (74 percent yield);

Elemental Analysis for $C_{17}H_{12}ClNO$: Calc.: C, 72.47; H, 4.29; N, 4.97 Found: C, 71.80; H, 4.27; N, 4.77.

1-(4-Fluorophenyl)-2-(5-chloro-2-pyrimidinyl)ethanone; a yellow solid melting at 154° C. (53 percent yield);

Elemental Analysis for $C_{12}H_8ClFN_2O$: Calc.: C, 57.50; H, 3.22; N, 11.18 Found: C, 57.99; H, 3.42; N, 10.93.

1-(4-Fluorophenyl)-2-(5-(trifluoromethyl)-2-pyrimidinyl)ethanone; a white solid melting at 97° C. (76 percent yield);

Elemental Analysis for $C_{13}H_8F_4N_2O$: Calc.: C, 54.94; H, 2.84; N, 9.86 Found: C, 55.09; H, 2.82; N, 9.87.

EXAMPLE 4

Preparation of
2-(5-Trifluoromethyl-2-Pyridinyl)-1-(4-Chlorophenyl)-2-Propen-1-One Acetic anhydride (19 mL, 21 g, 200 mmol) was added slowly to a stirring slurry of 2-(5-trifluoromethyl-2-pyridinyl)-1-(4-chlorophenyl)ethanone (12.1 g, 40.0 mmol) in bisdimethylaminomethane (22 mL, 16 g, 160 mmol) at 0° C. causing immediate solution. TLC showed complete conversion after 5 min and the mixture was partitioned between ether and water by adding these solvents and separating the layers. The organic layer was extracted with brine, dried over sodium sulfate, filtered, and evaporated under reduced pressure to obtain 13 g (99 percent of theory) of the title compound as a red oil.

1H NMR δ5.92 (s, 1), 6.73 (s, 1), 7.43 (d, 2, J=8.6), 7.64 (d, 1, J=8.3), 7.85 (d, 2, J=8.6), 7.92 (dd, 1, J=2.4, 8.3), 8.83 (m, 1).

The following were prepared similarly:

2-(6-Fluoro-2-pyridinyl)-1-(4-fluorophenyl)-2-propen-1-one; a red oil (97 percent yield).

2-(5-Trifluoromethyl-2-pyridinyl)-1-(4-fluorophenyl)-2--propen-1-one; a red oil ( 99 percent yield);

1H NMR δ5.90 (s, 1), 6.73 (s, 1), 7.12 (dd, 2, J=8.6, 8.6), 7.63 (d, 1, J=8.3) , 7.91 (dd, 1, J=2.3, 7.6), 7.94 (dd, 2, J=5.4, 8.9) , 8.83 (m, 1).

2-(5-Pyrimidinyl)-1-(4-fluorophenyl)-2-propen-1-one; an oil;

1H NMR δ5.9 (s, 1), 6.3 (s, 1), 7.1 (dd, 2), 7.9 (dd, 2), 8.8 (s, 2), 9.2 (s, 1).

2-(6-Chloro-3-quinolinyl)-1-phenyl-2-propen-1-one; a tan powder melting at 86°–87° C. (65 percent yield);

Elemental Analysis for $C_{18}H_{12}ClNO$: Calc.: C, 73.60; H, 4.12; N, 4.77 Found: C, 73.32; H, 4.14; N, 4.75.

2-(6-Chloro-2-quinolinyl)-1-(4-chlorophenyl)-2-propen-1-one; a tan powder melting at 117°–118° C. (50 percent yield);

Elemental Analysis for $C_{18}H_{11}Cl_2NO$: Calc.: C, 65.87; H, 3.38; N, 4.27 Found: C, 65.35; H, 3.38; N, 4.17.

2-(7-Chloro-3-quinolinyl)-1-phenyl-2-propen-1-one; an off-white powder melting at 95°–96° C. (69 percent yield);

Elemental Analysis for $C_{18}H_{12}ClNO$: Calc.: C, 73.60; H, 4.12; N, 4.77 Found: C, 74.54; H, 4.28; N, 4.70.

EXAMPLE 5

Preparation of 5-Methylsulfonyl-3-(Trifluoromethyl)Isothiazole

A. Preparation of Ethyl 5-Methylthio-3-(trifluoromethyl)isothiazole-4-carboxylate The general procedure of Krebs, *Aust. J. Chem.*, 42, 1291 (1989) was employed. Ethyl 3-amino-4,4,4-trifluorocrotonate (9.16 g, 50 mmol) was dissolved in 30 mL of N,N-dimethylformamide and 1.2 g of 60 percent in mineral oil sodium hydride (50 mmol) was added in small portions with stirring and cooling to keep the temperature around 25° C. The mixture was stirred for about 1 hr until the evolution of gas had essentially ceased and was then cooled to −7° C. Carbon disulfide (4.19 g, 55 mmol) in 4 mL of N,N-dimethylformamide was then added slowly with stirring maintaining the temperature below 10° C. by cooling. The mixture was then allowed to warm to 15° C. and 8.29 g (60 mmol) of iodomethane in 4 mL of N,N-dimethylformamide was added with stirring. After 15 min (minutes) the reaction mixture was poured onto 75 g of ice. The red oil that formed was extracted into 2×75 mL of ether. The ethereal solution was washed with saturated sodium chloride solution, dried over sodium sulfate, filtered, and concentrated by evaporation under reduced pressure and the residue was dissolved in 50 mL of ethanol and 7.91 g (100 mmol) of pyridine. A solution prepared by dissolving 12.7 g (50 mmol) of iodine and 20.75 g (125 mmol) of potassium iodide in 100 mL of water was added to this slowly with stirring. The precipitate that formed was collected by filtration and dissolved in ether. The ethereal solution was washed with water and 2×60 mL of 0.5N sodium thiosulfate solution, dried over sodium sulfate, filtered, and concentrated by evaporation under reduced pressure. The residue was recrystallized from hexane to obtain 5.7 g (42 percent of theory) of the title compound as a solid melting at 64°-65° C.

Elemental Analysis for $C_8H_8F_3NO_2S_2$: Calc.: %C, 35.4; %H, 2.97; %N, 5.16; %S, 23.6 Found: %C, 35.6; %H, 2.99; %N, 5.18; %S, 23.7.

B. Preparation of 5-Methylthio-3-(trifluoromethyl)isothiazole-4-carboxylic Acid

A 5.2 g (19.2 mmol) sample of ethyl 5-methylthio-3-(trifluoromethyl)isothiazole-4-carboxylate was combined with 1.39 g (21 mmol) of 85 percent potassium hydroxide and 25 mL of 95 percent ethanol and the mixture was heated on a steam bath for 45 min and then concentrated under reduced pressure to remove the volatiles. The residue was dissolved in water and acidified with concentrated hydrochloric acid. The white precipitate that formed was collected by filtration and dissolved in a mixture of acetone and ether. The resulting solution was dried over sodium sulfate, filtered, and concentrated by evaporation under reduced pressure to obtain 3.75 g (80 percent of theory) of the title compound as a white solid melting at 260°-262° C.

Elemental Analysis for $C_6H_4F_3NO_2S_2$: Calc.: %C, 29.6; %H, 1.66; %N, 5.76; %S, 26.4 Found: %C, 29.7; %H, 1.62; %N, 5.73; %S, 26.3.

C. Preparation of 5-Methylthio-3-(trifluoromethyl)isothiazole

5-Methylthio-3-(trifluoromethyl)isothiazole-4-carboxylic acid (9.4 g, 39 mmol) was dissolved in 15 mL of quinoline and 0.6 g (4.2 mmol) of cuprous oxide was added. The mixture was heated at 170° C. for about 30 min and then allowed to cool. It was then diluted with ether and the resulting solution was washed with 100 mL of 2N hydrochloric acid, dried over sodium bicarbonate, filtered, and distilled to obtain 6.55 g (85 percent of theory) of the title compound as a colorless liquid boiling at 126°-127° C. at 84 mm Hg (11 kiloPascals (kPa)) pressure.

Elemental Analysis for $C_5H_4F_3NS_2$: Calc.: %C, 30.1; %H, 2.02; %N, 7.03; %S, 32.2 Found: %C, 30.3; %H, 1.88; %N, 7.03; %S, 32.3.

D. Preparation of 5-Methylsulfonyl-3-(trifluoromethyl)isothiazole

A 2.0 g (10 mmol) sample of 5-methylthio-3-(trifluoromethyl)isothiazole was added to 5 mL of trifluoroacetic acid and the solution was heated to 50° C. Thirty percent hydrogen peroxide (0.85 g, 25 mmol) was then added slowly with stirring at 50°-60° C. and heating was continued for about 45 min. The mixture was next poured onto 40 g of ice and the precipitate that formed was collected by filtration. It was then dissolved in dichloromethane and the solution dried over magnesium sulfate, filtered, and concentrated by evaporation under reduced pressure to obtain a solid residue. This was diluted with hexane and then recovered by filtration and dried to obtain 1.6 g (69 percent of theory) of the title compound as a white solid melting at 93°-94° C.

Elemental Analysis for $C_5H_4F_3NO_2S_2$: Calc.: %C, 26.0; %H, 1.74; % N, 6.06; %S, 27.7 Found: %C, 26.0; %H, 1.65; % N, 6.03; %S, 27.8.

EXAMPLE 6

Preparation of 1-(4-Chlorophenyl)-2-(3-(Trifluoromethyl)-5-Isothiazolyl)Ethanone The oil of a 4.0 g (100 mmol) portion of 60 percent in mineral oil sodium hydride was removed by triple extraction with hexane and was replaced with 100 mL of tetrahydrofuran. 4-Chloroacetophenone (4.33 g, 28 mmol) was added and the mixture was heated at reflux with stirring for 1 hr and then allowed to cool. 5-Methylsulfonyl-3-(trifluoromethyl)isothiazole (4.57 g, 19.8 mmol) dissolved in a small amount of tetrahydrofuran was added and the mixture was heated at reflux with stirring for 3 hr and then allowed to cool. The mixture was next acidified with 60 mL of 10 percent acetic acid and the layers that formed were separated. The aqueous layer was extracted with 2×100 mL of ether and the organic fractions were combined, washed with sodium bicarbonate solution, dried over sodium sulfate, filtered, and concentrated by evaporation under reduced pressure to obtain a residue. This residue was washed with hexane and crystallized from a 1:1 mixture of dichloromethane and hexane to obtain 3.19 g (53 percent of theory) of the title compound as a solid melting at 109°-110° C.

Elemental Analysis for $C_{12}H_7ClF_3NOS$: Calc.: %C, 47.1; %H, 2.31; % N, 4.58; %S, 10.5 Found: %C, 47.4; %H, 2.42; % N, 4.56; %S, 10.3.

The following compounds were prepared similarly from 5-methylsulfonyl-3-(trifluoromethyl)isothiazole and an appropriately substituted acetophenone:

1-(4-fluorophenyl)-2-(3-(trifluoromethyl)-5-isothiazolyl)ethanone, a solid melting at 103°-105° C. (59 percent yield);

Elemental Analysis for $C_{12}H_7F_4NOS$: Calc.: %C, 49.8; %H, 2.24; % N, 4.84; %S, 11.1 Found: %C, 49.8; %H, 2.33; % N, 4.81; %S, 11.4; and 1-(4-(trifluoromethyl)phenyl)-2-(3-(trifluoromethyl)-5-isothiazolyl)ethanone, a solid melting at 114°-115° C. (48 percent yield);

Elemental Analysis for $C_{13}H_7F_6NOS$: Calc.: %C, 46.0; %H, 2.08; % N, 4.13; %S, 9.45 Found: %C, 46.1; %H, 2.14; % N, 4.21; %S, 9.54.

EXAMPLE 7

Preparation of 2-(3-Methyl-5-Isoxazolyl)-1-Phenylethanone

The general procedure of Micetich, *Can. J. Chem.*, 48, 2006 (1970) was employed. 3,5-Dimethylisoxazole (4.86 g, 50 mmol) and 100 mL of tetrahydrofuran were placed in a flask under nitrogen and cooled to −70° C. with an ether Dry Ice bath. To this was added with cooling and stirring 20 mL (50 mmol) of 2.5M n-butyl lithium in hexane solution at a rate such that the temperature remained below −50° C. and the mixture was allowed to stir at −70° C. for 1 hr. Benzonitrile (5.67 g, 55 mmol) was then added and stirring at −70° C. was continued for an additional 2-hr period. The resulting mixture was allowed to warm to ambient temperature and was then concentrated by evaporation under reduced pressure. The residue was mixed with 100 mL of hydrochloric acid and extracted with diohloromethane. The organic extract was dried over magnesium sulfate, filtered, and concentrated by evaporation under reduced pressure to obtain a solid residue which was recrystallized from ether to obtain 4.6 g (46 percent of theory) of the title compound as a yellow solid melting at 73°-74 ° C.

Elemental Analysis for $C_{12}H_{11}NO_2$: Calc.: %C, 71.6; %H, 5.51; % N, 6.96 Found: %C, 71.8; %H, 5.80; % N, 7.09.

The following were prepared similarly from 3,5-dimethylisoxazole and a substituted benzonitrile:

1-(4-chlorophenyl)-2-(3-methyl-5-isoxazolyl)ethanone, yellow crystals melting at 107°-109° C. (47 percent yield);

Elemental Analysis for $C_{12}H_{10}ClNO_2$: Calc.: %C, 61.2; %H, 4.28; % N, 5.94 Found: %C, 61.1; %H, 4.62; % N, 6.00; and 1-(4-fluorophenyl)-2-(3-methyl-5-isoxazolyl)ethanone, tan plates melting at 92°-93° C. (57 percent yield);

Elemental Analysis for $C_{12}H_{10}FNO_2$: Calc.: %C, 65.8; %H, 4.60; % N, 6.39 Found: %C, 65.7; %H, 4.69; % N, 6.69.

EXAMPLE 8

Preparation of 5-Methyl-2-Trifluoromethyloxazole

Aminoacetone hydrochloride of about 80 percent purity (13.3 g, 121 mmol) was slurried in 100 mL of benzene and 22 mL (146 mmol) of trifluoroacetic anhydride was added with stirring. The mixture was heated at reflux for 2-3 hr during which time it separated into two liquid phases and was then allowed to cool. Sufficient diatomaceous earth was added to sequester the smaller lower phase as a white solid. This was collected by filtration and extracted with 2×50 mL of dichloromethane. The upper phase and the dichloromethane extracts were combined and distilled at 200 torr (27 kPa) through a short Vigreaux column until the head temperature reached 70° C. The residue was then kugelrohr distilled taking the fraction that distilled at 110° C. and 20 tort (2.7 kPa). This material, which solidified, was dissolved in 50 mL of phosphorus oxychloride and the mixture was heated at reflux for 2 hr during which time it turned very dark. The mixture was then distilled through a 15 cm Vigreaux column until the head temperature reached 110° C. The distillate, a water-white oil, was slowly added to 150 mL of water with vigorous stirring, keeping the temperature below 40° C. After 30 min the mixture was extracted with 3×50 mL of ether. The ethereal extract was dried over magnesium sulfate and distilled using a 30 cm glass helices packed column to remove the ether and other volatiles. Solid sodium bicarbonate was cautiously added to the residue until foaming ceased. The resulting slurry was filtered and the solids extracted with 3 mL of ether. The combined organics were distilled through a short Vigreaux column to obtain 1.75 g (9 percent of theory) of the title compound as a colorless oil containing about 10 percent ether as an impurity boiling at 100°-104° C. The proton NMR spectrum had absorptions at δ2.36 (s, 3H) and 6.85 (s, 1H).

EXAMPLE 9

Preparation of 5-Bromomethyl-2-Trifluoromethylthiazole

A. Preparation of Trifluoroacetamidoacetone

Aminoacetone hydrochloride (13.29 g, 121 mmol) was slurried in 200 mL of dichloromethane and stirred vigorously as 22 mL (146 mmol) of trifluroacetic acid was added. The mixture was heated to reflux with stirring for about I hr at which time the evolution of gas had ceased. The resulting mixture was concentrated by evaporation at 60° C. and the residue was dissolved in 200 mL of ether. Solid sodium bicarbonate was cautiously added with stirring until foaming ceased. The resulting slurry was filtered through a 2×5 cm silica gel plug and the plug was eluted with an additional 100 mL of ether. The combined filtrates were concentrated by evaporation at temperatures up to 60° C. The residue was kugelrohr distilled at a pot temperature of 100°-110° C. and a pressure of 18 torr (2.4 kPa) to obtain 9.7 g (47 percent of theory) of the title compound as a waxy white solid. An analytical sample prepared by recrystallization from pentane was a white solid melting at 71°-73° C.

Elemental Analysis for $C_5H_6F_3NO_2$: Calc.: %C, 35.5; %H, 3.58; % N, 8.28 Found: %C, 35.6; %H, 3.69; % N, 8.22.

B. Preparation of 5-Methyl-2-trifluoromethylthiazole

Trifluoroacetamidoacetone (8.45 g, 50 mmol) and 20.2 g (50 mmol) of Lawesson's reagent were slurried in 100 mL of benzene and the mixture heated at reflux with stirring for 4–5 hr to obtain a clear solution. This was allowed to cool and was washed with 50 mL of 10 percent aqueous sodium hydroxide solution, dried over magnesium sulfate, and filtered. The resulting solution was kugelrohr distilled at 160° C. and the distillate was distilled through a 40 cm column packed with glass helices (to remove the benzene) until the head temperature began to drop. It was then distilled through a 20 cm Vigreauz column to obtain 5.1 g (61 percent of theory) of the title compound as a pale oil boiling at 138°-141° C.

Elemental Analysis for $C_5H_4F_3NS$: Calc.: %C, 35.9; %H, 2.41; % N, 8.38; %S, 19.2 Found: %C, 36.1; %H, 2.55; % N, 8.53; %S, 18.9.

C. Preparation of 5-Bromomethyl-2-trifluoromethylthiazole

5-Methyl-2-trifluoromethylthiazole (2.26 g, 13.5 mmol), N-bromosuccinimide (2.64 g, 14.6 mmol), and 50 mL of benzene were placed in a jacketed flask and the resulting mixture was stirred and irradiated with a 250 Watt sun lamp placed 10 cm from the flask. The temperature rose from 25° to 40° C. After 3 hr an additional 0.26 g (1.5 mmol) of N-bromosuccinimide was added and the reaction continued another 30 min. Analysis of an aliquot by gas-liquid chromatography indicated that the mixture contained about 7 percent starting material, 73 percent title compound, and 17 percent dibrominated material. The mixture was extracted with 50 mL of 2 percent aqueous sodium hydroxide, dried over magnesium sulfate, filtered, and concentrated by evaporation under reduced pressure to obtain a yellow oil. This was purified by medium pressure liquid chromatography to obtain 1.86 g (56 percent of theory) of 5-bromomethyl-2-trifluoromethylthiazole as a pale yellow oil which was 97 percent pure by gas liquid chromatography. The proton NMR spectrum had absorptions at δ4.69 (s, 2H) and 7.87 (s, 1H).

5-Bromomethyl-2-trifluoromethyloxazole, which has a boiling point at 80°-90° C. under 25 torr (3.3 kPa) pressure, was prepared similarly and was recovered in 38 percent yield as an 85 percent pure compound containing 12 percent dibromo compounds and 2.5 percent benzene. The proton NMR spectrum had absorptions at δ4.47 (s, 2H) and 7.20 (s, 1H).

EXAMPLE 10

Preparation of
1-(4-Fluorophenyl-2-(2-Trifluoromethyl-5-Thiazolyl-)Ethanone

A solution of 2.4M n-butyl lithium in hexane (6.4 mL, 15.4 mmol) was added to a solution of 2.15 mL (15.4 mmol) of diisopropylamine in 50 mL of dry tetrahydrofuran −10° C. under nitrogen with stirring over a 2-min period. The resulting solution was cooled to −70° C. and a solution containing 3.18 g (14 mmol) of 2-(trimethylsilyloxy)-2-(4′-fluorophenyl)acetonitrile in 3 mL of dry tetrahydrofuran was added dropwise by means of a syringe pump over a 20-min period under nitrogen with stirring. The resulting bright yellow solution was stirred for an additional 30 min at −70° C. or below and then a solution of 2.92 g (11.9 mmol) of 5-bromomethyl-2-trifluoromethylthiazole in 5 mL of dry tetrahydrofuran was added over 30 min under nitrogen with stirring to obtain a dark, thick slurry. After a 45-min reaction period this mixture was allowed to warm and was poured into a rapidly stirred mixture consisting of 25 mL of 10 percent aqueous hydrochloric acid and 10 mL of methanol. A 0.5 mL portion of 48 percent aqueous hydrofluoric acid was then added and the mixture stirred until all of the trimethylsilane protecting group was removed. Sufficient 10 percent aqueous sodium hydroxide was added with stirring to adjust the pH to about 10 and after 15 min the phases were separated. The aqueous phase was extracted with 2×30 mL of ether and the combined organic phases were washed with 50 mL of 10 percent aqueous hydrochloric acid and 50 mL of saturated aqueous sodium chloride, dried over magnesium sulfate, and concentrated by evaporation under reduced pressure. The residue was kugelrohr distilled, first at 70° C. and 0.05 torr (6.7 Pa (Pascals)) to remove 4-fluorobenzaldehyde and then at 100°-110° C. and 0.05 tort (6.7 Pa) to distill 2.93 g (85 percent of theory) of the title compound, which was obtained as a waxy yellow solid of 95 percent purity by gas liquid chromatography. An analytical sample obtained by crystallization from a mixture of hexane and acetone melted at 66.5°-68.5° C.

Elemental Analysis for $C_{12}H_7F_4NOS$: Calc.: %C, 49.8; %H, 2.44; % N, 4.84; %S, 11.1 Found: %C, 50.1; %H, 2.44; % N, 4.92; %S, 11.5.

1-(4-Fluorophenyl-2-(2-trifluoromethyl-5-oxazolyl)ethanone was prepared similarly and was obtained as a yellow oil that distilled at 80° C. and 0.02 torr (2.7 Pa) pot temperature.

Elemental Analysis for $C_{12}H_7F_4NO_2$: Calc.: %C, 52.8; %H, 2.58; % N, 5.13 Found: %C, 52.7; %H, 2.77; % N, 5.10.

EXAMPLE 11

Preparation of
3-(4-Chlorophenyl)-4,5-Dihydro-N-(4-Trifluoromethoxyphenyl)-4-(3-Trifluoromethyl-5-Isothiazolyl)-1H-Pyrazole-1-Carboxamide A mixture of 5.0 mL of N,N,N′, N′-tetramethyldiaminomethane and 3.06 g (10 mmol) of 1-(4-chlorophenyl)-2-(3-(trifluoromethyl)-5-isothiazolyl)ethanone were combined and chilled in an ice-salt bath to about 0° C. A 5.0 mL portion of acetic anhydride was added dropwise with stirring maintaining the temperature at less than 20° C. with cooling and the reaction was continued for an additional 45 min at which time the mixture was poured onto 40 g of ice. The oil that formed was recovered by extraction with 3×50 mL of ether and the ethereal extracts were combined, washed with aqueous sodium bicarbonate and aqueous sodium chloride solutions, dried over sodium sulfate, filtered, and concentrated by evaporation under reduced pressure to obtain 3 g of a glassy material. This was dissolved in 15 mL of trifluoroacetic acid with cooling to 0° C. and 1.41 g (28 mmol) of hydrazine monohydrate was added with stirring. After 2 min stirring the mixture was diluted with ice water and filtered to recover the solid 3-(4-chlorophenyl)-4,5-dihydro-4-(3-trifluoromethyl-5-isothiazolyl)-1H-pyrazole that formed. This was dissolved in dichloromethane and the solution obtained was dried over sodium bicarbonate and sodium sulfate and was filtered. 4-Trifluoromethoxyphenyl isocyanate (1.91 g, 9.4 mmol) was added dropwise with stirring at ambient temperature and the resulting mixture was allowed to stand overnight. A 1.5 mL portion of acetic acid was added and the mixture was stirred for 30 min at which time it was washed with aqueous sodium bicarbonate solution, dried over sodium sulfate, filtered, and concentrated by evaporation under reduced pressure to obtain an oil. The residual oil was placed on a silica gel column and eluted with a 9:1 mixture of hexane and acetone to obtain 0.45 g (8.4 percent of theory) of the title compound as a solid melting at 101°-104° C.

Elemental Analysis for $C_{21}H_{13}ClF_6N_4O_2S$: Calc.: %C, 47.2; %H, 2.45; % N, 10.5; %S, 6.00 Found: %C, 47.2; %H, 2.67; % N, 10.2; %S, 6.10.

The following were prepared similarly from a 1-(substituted-phenyl)-2-(3-(trifluoromethyl)-5-isothiazolyl)ethanone and an isocyanate:

4,5-dihydro-3-(4-fluorophenyl)-4-(3-trifluoromethyl-5-isothiazolyl)-N-(4-trifluoromethylphenyl)-1H-pyrazole-1-carboxamide, a white solid melting at 158°-159° C. (30 percent yield);

Elemental Analysis for $C_{21}H_{13}F_7N_4OS$: Calc.: %C, 50.2; %H, 2.61; % N, 11.2; %S, 6.38 Found: %C, 50.6; %H, 2.76; % N, 11.1; %S, 6.06; and 4,5-dihydro-N-(4-trifluoromethoxyphenyl)-4-(3-trifluoromethyl-5-isothiazolyl)-3-(4-trifluoromethylphenyl)-1H-pyrazole-1-carboxamide, a white solid melting at 165°-166° C. (11 percent yield);

Elemental Analysis for $C_{22}H_{13}F_9N_4O_2S$: Calc.: %C, 46.5; %H, 2.30; % N, 9.86; %S, 5.64 Found: %C, 46.4; %H, 2.30; % N, 9.71; %S, 5.30.

EXAMPLE 12

Preparation of
4,5-Dihydro-4-(3-Methyl-5-Isoxazolyl)-3-Phenyl-N-(4-Trifluoromethoxyphenyl)-1H-Pyrazole-1-Carboxamide A mixture of 20 mL of dichloromethane, 2.01 g (10 mmol) of 2-(3-methyl-5-isoxazolyl)-1-phenylethanone and 1.12 g (11 mmol) of N,N,N',N'-tetramethydiaminomethane was prepared and cooled to −15° C. and 1.25 g (11 mmol) of trifluoroacetic acid in 5 mL of dichloromethane was added with cooling and stirring. Stirring was continued for 5 min at about 0° C. and then the mixture was allowed to warm to ambient temperature and stir for another 1.75 hr. A proton NMR spectrum of the mixture was taken which indicated complete disappearance of the starting material. Anhydrous hydrazine (0.96 g, 30 mmol) was added and the mixture was allowed to react with stirring for 2 hr. A proton NMR spectrum of the mixture indicated complete conversion to 4,5-dihydro-4-(3-methyl-5-isoxazolyl)-3-phenyl-1H-pyrazole. The mixture was washed with saturated aqueous sodium bicarbonate solution, dried over sodium sulfate, and filtered. 4-(Trifluoromethoxy)phenyl isocyanate (2.19 g, 10.8 mmol ) was then added with stirring. The mixture was allowed to react for 1 hr and then 1 mL of acetic acid was added and the mixture was allowed to react for 5 min. It was then washed with saturated aqueous sodium bicarbonate, dried over sodium sulfate, filtered, and concentrated by evaporation under reduced pressure. The resulting solid was extracted with boiling ether and air dried to obtain 3.1 g (72 percent of theory) of the title compound as a white solid melting at 195°-197° C.

Elemental Analysis for $C_{21}H_{17}F_3N_4O_3$: Calc.: %C, 58.7; %H, 3.97; % N, 13.0 Found: %C, 58.4; %H, 4.25; % N, 13.0.

EXAMPLE 13

Preparation of
4,5-Dihydro-3-(4-Fluorophenyl)-N-(4-Trifluoromethylphenyl)-4-(2-Trifluoromethyl-5-Thiazolyl)-1H-Pyrazole-1-Carboxamide A solution of 112 uL (microliters) (1.1 mmol) of acetic anhydride and 289 mg (milligram) (1.0 mmol) of 1-(4-fluorophenyl)-2-(2-trifluoromethyl-5-thiazolyl)ethanone in 2 mL of chloroform was added to a solution of 136 uL (1.2 mmol) of N,N,N',N'-tetramethyldiaminomethane in 3 mL of chloroform with stirring over a 5-min period. The resulting solution was stirred for 10 min and then 46 uL (1.5 mmol) of anhydrous hydrazine and one drop of trifluoroacetic acid were added sequentially. The mixture was heated at reflux with stirring for 20-30 min and then was cooled and diluted to 20 mL with dichloromethane. The resulting solution was washed with 2×10 mL of water, dried over sodium sulfate, and filtered to obtain 4,5-dihydro-3-(4-fluorophenyl)-4-(2-trifluoromethyl-B-thiazolyl)-1H-pyrazole. 4-Trifluoromethylphenyl isocyanate (143 uL, 1.0 mmol) was then added and the mixture was heated at reflux for 15 min, cooled, and concentrated by evaporation under reduced pressure. The residue was purified by medium pressure liquid chromatography eluting with a 90:10 mixture of hexane and ether to obtain 297 mg (63 percent of theory) of the title compound as a white foamy solid. An analytical sample prepared by recrystallization from a mixture of hexane and acetone was a white solid melting at 174°-176° C.

Elemental Analysis for $C_{21}H_{13}F_7N_4OS$: Calc.: %C, 50.2; %H, 2.61; % N, 11.2; %S, 6.38 Found: %C, 50.1; %H, 2.51; % N, 11.1; %S, 6.39.

The following compounds were prepared similarly from 1-(4-chlorophenyl)-2-(2-trifluoromethyl-5-thiazolyl)ethanone and 1-(4-fluorophenyl)-2-(2-trifluoromethyl-5-oxazolyl)ethanone:

N-(4-chlorophenyl)-4,5-dihydro-3-(4-fluorophenyl)-4-(2-trifluoromethyl-5-thiazolyl)-1H-pyrazole-1-carboxamide, a white solid melting at 187.5°-189.5° C. (57 percent yield);

Elemental Analysis for $C_{20}H_{13}ClF_4N_4OS$: Calc.: %C, 51.2; %H, 2.79; % N, 12.0; %S, 6.84 Found: %C, 51.2; %H, 2.82; % N, 11.7; %S, 6.63;

4,5-dihydro-3-(4-fluorophenyl)-4-(2-trifluoromethyl-5-oxazolyl)-N-(4-trifluoromethylphenyl)-1H-pyrazole-1-carboxamide, a white solid melting at 178.5°-180.5° C. (39 percent yield);

Elemental Analysis for $C_{21}H_{13}F_7N_4O_2$: Calc.: %C, 51.9; %H, 2.69; % N, 11.5 Found: %C, 51.5; %H, 2.78; % N, 11.6.

EXAMPLE 14

Preparation of
2-(5-Chloro-2-Thiazolyl)-1-(4-Fluorophenyl)Propanone

4-Fluoropropiophenone (3.04 g, 20 mmol) was added over a 10-min period to a slurry of potassium hydride (5.5 g of 35 percent in oil washed 3 times with hexanes (48 mmol)) in 50 mL of dry tetrahydrofuran at ambient temperature with stirring under nitrogen. The mixture was allowed to react for 15 min and was then cooled to 0° to −10° C. 2,5-Dichlorothiazole (3.39 g, 22 mmol) was then added over a 15-min period with stirring and the reaction allowed to proceed under those conditions for 8 hr. The resulting mixture was extracted with water, dried over magnesium sulfate, filtered, and concentrated by evaporation under reduced pressure. The residue was kugelrohr distilled at 100°-110° C. and 0.02 torr (2.7 Pa) pressure to obtain 4.71 g (87 percent of theory) of the title compound as a yellow oil which tended to darken on standing.

Elemental Analysis for $C_{12}H_9ClFNOS$: Calc.: %C, 53.4; %H, 3.36; % N, 5.19; %S, 11.9 Found: %C, 54.6; %H, 3.91; % N, 5.24; %S, 11.2.

EXAMPLE 15

Preparation of
2-(5-Chloro-2-Thiazolyl)-1-(4-Fluorophenyl)-2-(Phenylselenenyl)Propanone A solution of 1.35 g (5.0 mmol) of 2-(5-chloro-2-thiazolyl)-1-(4-fluorophenyl)propanone in 2 mL of dry tetrahydrofuran was added over a 10-min period to a slurry of sodium hydride (240 mg of 60 percent in oil washed 3 times with hexane (6.0 mmol)) in 30 mL of dry tetrahydrofuran with stirring under nitrogen. The resulting mixture was cooled to −70° C. and 1.15 g (6.0 mmol) of phenylselenenyl chloride (recrystallized from hexanes shortly before use) dissolved in 5 mL of tetrahydrofuran was added by means of a dropping funnel with stirring under nitrogen over a 10-min period. The mixture was allowed to warm to ambient temperature and was then extracted with water, dried over magnesium sulfate, filtered, and concentrated by evaporation under reduced pressure. The residual oil was purified by medium pressure liquid chromatography eluting with a 9:1 mixture of hexanes and ethyl acetate to obtain 1.68 g (79 percent of theory) of the title compound as a yellow oil.

EXAMPLE 16

Preparation of 4-(5-Chloro-2-Thiazolyl)-4,5-Dihydro-3-(4-Fluorophenyl)-N-(4-Trifluoromethylphenyl)-1H-pyrazole-1-carboxamide A slurry of dried metachloroperbenzoic acid (861 mg of 50–60 percent purity (2.5 mmol)) in 10 mL of dichloromethane was added to a solution of 1.06 g (2.5 mmol) of 2-(5-chloro-2-thiazolyl)-1-(4-fluorophenyl)-2-(phenylselenenyl)propanone in 25 mL of dichloromethane at −50° C. under nitrogen with stirring. The mixture was allowed to warm to −25° C. for a few minutes and was then cooled to −60° C. and pressure filtered. The filtrate was allowed to warm to −25° C. for a few minutes. It was then cooled to −60° C. and 160 uL (5.0 mmol) of anhydrous hydrazine was added with vigorous stirring. The mixture was allowed to warm to −25° C. for about 30 min and then 1 mL of trifluoroacetic acid was added and the reaction was allowed to proceed for another 20 min. The resulting solution was extracted with 50 mL of water and 50 mL of saturated aqueous sodium bicarbonate, dried over sodium sulfate and filtered to obtain 4-(5-chloro-2-thiazolyl)-4,5-dihydro-3-(4-fluorophenyl)-1H-pyrazole. The solution was then treated with 372 mg (2.0 mmol) of 4-trifluoromethylphenyl isocyanate at reflux with stirring for 15 min. The resulting mixture was allowed to cool, extracted with water, dried over sodium sulfate, filtered, and concentrated by evaporation under reduced pressure. The residual oil was purified by medium pressure liquid chromatography eluting with a 9:1 mixture of hexanes and ether to obtain a solid which was recrystallized from a mixture of hexanes and acetone to obtain 150 mg (13 percent of theory) of the title compound as a white solid melting at 187.5°–189° C.

Elemental Analysis for $C_{20}H_{13}ClF_4N_4OS$: Calc.: %C, 51.2; %H, 2.79; % N, 12.0; %S, 6.84 Found: %C, 51.3; %H, 2.91; % N, 12.0; %S, 6.54.

EXAMPLE 17

Preparation of 3-(4-Chlorophenyl)-4,5-dihydro-4-(5-trifluoromethyl-2-pyridinyl)-1H-pyrazole Hydrazine hydrate (7.8 mL, 8.0 g, 160 mmol) was added slowly dropwise to a stirring solution of 2-(5-trifluoromethyl-2-pyridinyl)-1-(4-chlorophenyl)-2-propen-1-one in N,N-dimethylformamide (DMF) (40 mL) at 21° C. TLC showed complete conversion after 1 hr and the mixture was added dropwise with vigorous stirring to ice water to obtain a fluffy pale precipitate and a dark red-brown precipitate. The precipitates were collected by filtration and washed with water to obtain 14 g of solids. 1H NMR showed the two solids to be identical and to contain the title compound in 28 percent of theory yield.

1H NMR δ3.73 (dd, 1, J=4.1, 9.8), 4.04 (dd, 1, J=10.2, 10.2), 4.78 (dd, 1, J=4.1, 11.0), 7.2–8.0 (m, 6), 8.8 (br s, 1).

The following were prepared similarly: 4,5-dihydro-3-(4-fluorophenyl)-4-(6-fluoro-2-pyridinyl)-1H-pyrazole; a white solid (DMF solvent, 56 percent yield);

4,5-dihydro-3-(4-fluorophenyl)-4-(5-trifluoromethyl-2-pyridinyl)-1H-pyrazole; a white solid (DMF solvent, 28 percent yield);

4,5-dihydro-3-(4-chlorophenyl)-4-(5-(trifluoromethyl)-2-pyridinyl)-1H-pyrazole; (DMF solvent);

4,5-dihydro-3-(4-chlorophenyl)-4-(5-cyano-2-pyridinyl)-1H-pyrazole; (trifluoroacetic acid solvent);

4,5-dihydro-3-(4-fluorophenyl)-4-(3-fluoro-5-(trifluoromethyl)-2-pyridinyl)-1H-pyrazole; (2-methylpyrazine and 3-chloropyridine solvents);

4,5-dihydro-3-phenyl-4-(3-pyridinyl)-1H-pyrazole; (DMF solvent);

4,5-dihydro-3-phenyl-4-(2,6-di(trifluoromethyl)-4-pyridinyl)-1H-pyrazole; (trifluoroacetic acid solvent);

4,5-dihydro-3-phenyl-4-(6-chloro-3-quinolinyl)-1H-pyrazole; (DMF solvent, 88 percent yield);

4,5-dihydro-3-phenyl-4-(7-chloro-3-quinolinyl)-1H-pyrazole; (DMF solvent, 85 percent yield);

3-(4-chlorophenyl)-4-(7-chloro-2-quinolinyl)-4,5-dihydro-1H-pyrazole; (trifluoroacetic acid solvent);

3-(4-chlorophenyl)-4-(6-chloro-2-quinolinyl)-4,5-dihydro-1H-pyrazole; (trifluoroacetic acid solvent);

4,5-dihydro-3-(4-fluorophenyl)-4-(5-pyrimidinyl)-1H-pyrazole; white solid (DMF solvent, 12 percent yield);

4,5-dihydro-3-phenyl-4-(5-pyrimidinyl)-1H-pyrazole; (DMF solvent);

4,5-dihydro-3-(4-fluorophenyl)-4-(5-chloro-2-pyrimidinyl)-1H-pyrazole; (trifluoroacetic acid solvent);

4,5-dihydro-3-(4-fluorophenyl)-4-(6-chloro-4-pyrimidinyl)-1H-pyrazole; (trifluoroacetic acid solvent);

4,5-dihydro-3-(4-fluorophenyl)-4-(6-chloro-4-pyrimidinyl)-1H-pyrazole; (trifluoroacetic acid solvent);

4,5-dihydro-3-(4-fluorophenyl)-4-(2-(trifluoromethyl)-5-pyrimidinyl)-1H-pyrazole; (trifluoroacetic acid solvent);

4,5-dihydro-3-(4-fluorophenyl)-4-(5-trifluoromethyl-2-pyrazinyl)-1H-pyrazole; (trifluoroacetic acid solvent);

4-(6-chloro-2-pyrazinyl)-4,5-dihydro-3-(4-fluorophenyl)-1H-pyrazole; (trifluoroacetic acid solvent); and 3-(4-chlorophenyl)-4-(6-chloro-3-pyridazinyl)-4,5-dihydro-1H-pyrazole; (trifluoroacetic acid solvent).

Elemental Analysis for $C_{21}H_{16}ClF_3N_4O_3$: Calc.: %C, 56.3; %H, 3.60; % N, 12.5 Found: %C, 56.4; %H, 3.83; % N, 12.5.

EXAMPLE 18

Preparation of 3-(4-Chlorophenyl)-4,5-Dihydro-N-(4-(Methylthio)-phenyl)-4-(5-Trifluoromethyl-2-Pyridinyl)-1H-Pyrazole-1-Carboxamide 4-(Methylthio)phenyl isocyanate (2.8 g, 17 mmol) was added to a stirring slurry of 3.8 g (3.0 mmol) of 3-(4-chlorophenyl)-4,5-dihydro-4-(5-trifluoromethyl-2-pyridinyl)-1H-pyrazole in dichloromethane (25 mL) at 21° C. causing rapid formation of a pale precipitate. TLC showed complete conversion after 19 hr and the precipitate, which was the corresponding bisaryl urea, was removed by gravity filtration. The filtrate was diluted with saturated aqueous sodium bicarbonate and the layers separated. The organic layer was dried over sodium sulfate, filtered, and evaporated to obtain a red oil which solidified on standing. This was purified by column chromatography eluting with 100:0 to 90:10 methylene chloride/ethyl acetate solvent. The product was recrystallized by dissolving in ethyl acetate and then adding hexane to obtain 0.44 g (29 percent of theory; 9 percent from the ethanone) of the title compound as fine white needles melting at 225°–226° C.;

Molecular ion in mass spectrum: 490;

IR absorptions at 3400, 1673, 1583, 1525, 1328, 1145, 1133, and 835 cm$^{-1}$;

1H NMR $\delta$2.45 (s, 3), 4.22 (dd, 1, J=5.3, 11.6), 4.47 (dd, 1, J=11.8, 11.8), 5.01 (dd, 1, J=5.3, 11.9), 7.25 (d, 2, J=8.7), 7.28 (d, 2, J=8.7), 7.32 (d, 1, J=8.2), 7.47 (d, 2, J=8.7), 7.58 (d, 2, J=8.7), 7.86 (dd, 1, J=2.0, 8.2), 8.03 (br s, 1), 8.80 (m, 1); 13C NMR $\delta$16.98, 53.22, 53.25, 119.82, 120.19, 121.73, 125.83 (q, J=67), 126.02 (q, J=301), 128.12, 128.46, 128.65, 129.08, 132.24, 134.75 (q, J=3), 136.01, 136.19, 147.00 (q, J=4), 151.63, 152.34, 163.13.

Elemental Analysis for $C_{23}H_{18}ClF_3N_4OS$: Calc.: C, 56.27; H, 3.70; N, 11.41 Found: C, 56.82; H, 3.76; N, 11.64.

What is claimed is:

1. A 3,4-disubstituted-4,5-dihydro-1H-pyrazole compound of the formula

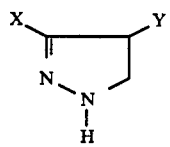

wherein

Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety wherein said substituents are selected from F, Cl, Br, CN, COQ, $CF_3$, OR', SR', $NO_2$, and OAr or a 5-membered aromatic heterocyclic ring moiety containing one ring oxygen or sulfur atom and one or two ring nitrogen atoms, which moiety is optionally substituted with one substituent selected from F, Cl, Br, CN, COQ, R, OR', SR', SOR', $SO_2R'$, $NO_2$, and OAr and, in those moieties containing only one ring nitrogen atom, optionally additionally substituted with a F substituent;

X represents phenyl optionally substituted in the 4-position with F, Cl, Br, CN, COQ, R, OR', SR', SOR', $SO_2R'$, $NO_2$, or OAr and/or in the 3-position with F, Cl, Br, CN, R, or OR';

Q represents OR'', SR'', $NH_2$, NHR'', or NR''$_2$;

R represents $C_1$–$C_3$ alkyl, $C_2$–$C_3$ alkenyl, or $C_2$–$C_3$ alkynyl optionally singly to completely substituted with fluorine or chlorine;

R' represents $C_1$–$C_3$ alkyl optionally singly to completely substituted with fluorine or chlorine;

R'' represents $C_1$–$C_4$ alkyl, $C_3$–$C_4$ alkenyl, or $C_3$–$C_4$ alkynyl; and Ar represents phenyl optionally substituted with 1 or 2 compatible substituents selected from F, Cl, Br, CN, COQ, R, OR', SR', SOR', $SO_2R'$, and $NO_2$.

2. A compound according to claim 1 wherein X represents phenyl substituted in the 4-position with F, Cl, Br, $CF_3$, $OCF_3$, $OCF_2H$, $OCF_2CF_2H$, $SO_2CF_3$, or $SCF_3$.

3. A compound according to claim 2 wherein X represents 4-fluorophenyl.

4. A compound according to claim 1 wherein the Y moiety substituent is F, Cl, Br, CN, $CF_3$, $OCF_2H$, or $OCF_3$.

5. A compound according to claim 1 wherein Y represents a 5-substituted-2-pyridinyl or 5-substituted-2-pyrimidinyl moiety.

6. A compound according to claim 5: 4,5-dihydro-3-(4-fluorophenyl)-4-(5-trifluoromethyl-2-pyridinyl)-1H-pyrazole.

7. A compound according to claim 5: 4-(5-chloro-2-pyridinyl)-4,5-dihydro-3-(4-fluorophenyl)-1H-pyrazole.

8. A compound according to claim 5: 4,5-dihydro-3-(4-fluorophenyl)-4-(5-fluoro-2-pyridinyl)-1H-pyrazole.

9. A compound according to claim 5: 4-(5-cyano-2-pyridinyl)-4,5-dihydro-3-(4-fluorophenyl)-1H-pyrazole.

10. A compound according to claim 5: 4-(5-chloro-2-pyrimidinyl)-4,5-dihydro-3-(4-fluorophenyl)-1H-pyrazole.

11. A compound according to claim 5: 4,5-dihydro-3-(4-fluorophenyl)-4-(5-fluoro-2-pyrimidinyl)-1H-pyrazole.

12. A compound according to claim 1 wherein Y represents a thiazolyl or oxazoiyl moiety attached to the dihydropyrazole ring at one position adjacent to the oxygen or sulfur atom and possessing a substituent in the other position adjacent to the oxygen or sulfur atom.

13. A compound according to claim 12: 4-(5-chloro-2-thiazolyl)-4,5-dihydro-3-(4-fluorophenyl)-1H-pyrazole.

14. A process for preparing a 3,4-di-substituted-4,5-dihydro-1H-pyrazole compound of the formula

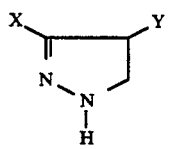

wherein

Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety wherein said substituents are selected from F, Cl, Br, CN, COQ, $CF_3$, OR', SR', $NO_2$, and OAr or a 5-membered aromatic heterocyclic ring moiety containing one ring oxygen or sulfur atom and one or two ring nitrogen atoms, which moiety is optionally substituted with one substituent selected from F, Cl, Br, CN, COQ, R, OR', SR', SOR', $SO_2R'$, $NO_2$, and OAr and, in those moieties containing only one ring nitrogen atom, optionally additionally substituted with a F substituent;

X represents phenyl optionally substituted in the 4-position with F, Cl, Br, CN, COQ, R, OR', SR', SOR', $SO_2R'$, $NO_2$, or OAr and/or in the 3-position with F, Cl, Br, CN, R, or OR';

Q represents OR'', SR'', $NH_2$, NHR'', or NR''$_2$;

R represents C$_1$-C$_3$ alkyl, C$_2$-C$_3$ alkenyl, or C$_2$-C$_3$ alkynyl optionally singly to completely substituted with fluorine or chlorine;

R' represents C$_1$-C$_3$ alkyl optionally singly to completely substituted with fluorine or chlorine;

R'' represents C$_1$-C$_4$ alkyl, C$_3$-C$_4$ alkenyl, or C$_3$-C$_4$ alkynyl; and Ar represents phenyl optionally substituted with 1 or 2 compatible substituents selected from F, Cl, Br, CN, COQ, R, OR', SR', SOR', SO$_2$R' and NO$_2$ which comprises combining an ethanone compound of the formula $$X-\underset{\underset{O}{\|}}{C}-CH_2-Y$$

wherein each of the substituents are defined as above in an optionally chlorinated hydrocarbon solvent with an approximately equimolar amount of an N,N,N',N'-tetra-(C$_1$-C$_3$)alkyldiaminomethane, dipiperidinomethane, dipyrrolidinylmethane or N,N',N''-tri(C$_1$-C$_3$)alkylhexahydro-1,3,5-triazine compound and an approximately equimolar amount of an acid or anhydride of the formula $$R^a-CO_2H \text{ or } (R^a-CO)_2O$$

wherein R$^a$ represents (C$_1$-C$_4$)alkyl or phenyl, each optionally monosubstituted to completely substituted with F or Cl, or H at about −10° C. to about 30° C. to obtain an intermediate Mannich adduct of the formula $$X-\underset{\underset{O}{\|}}{C}-\underset{CH_2 N((C_1-C_3)alkyl)_2}{\overset{}{C}}H-Y$$

wherein each of the substituents are defined as above, and, without isolation, adding hydrazine at about 0° C. to about 50° C., optionally in the presence of an added catalytic amount of a strong acid, to obtain said 3,4-disubstituted-4,5-dihydro-1H-pyrazole compound.

15. A process according to claim 14 wherein X represents phenyl substituted in the 4-position with F, Cl, Br, CF$_3$, OCF$_3$, OCF$_2$H, OCF$_2$CF$_2$H, SO$_2$CF$_3$, or SCF$_3$.

16. A process according to claim 15 wherein X represents 4-fluorophenyl.

17. A process according to claim 14 wherein the Y moiety substituent is F, Cl, Br, CN, CF$_3$, OCF$_2$H, or OCF$_3$.

18. A process according to claim 14 wherein Y represents a 5-substituted-2-pyridinyl or 5-substituted-2-pyrimidinyl moiety.

19. A process according to claim 18 wherein the compound produced is selected from 4,5-dihydro-3-(4-fluorophenyl)-4-(5-trifluoromethyl-2-pyridinyl)-1H-pyrazole, 4-(5-chloro-2-pyridinyl)-4,5-dihydro-3-(4-fluorophenyl)-1H-pyrazole, 4,5-dihydro-3-(4-fluorophenyl)-4-(5-fluoro-2-pyridinyl)-1H-pyrazole, 4-(5-cyano-2-pyridinyl)-4,5-dihydro-3-(4-fluorophenyl)-1H-pyrazole, 4-(5-chloro-2-pyrimidinyl)-4,5-dihydro-3-(4-fluorophenyl)-1H-pyrazole, and 4,5-dihydro-3-(4-fluorophenyl)-4-(5-fluoro-2-pyrimidinyl)-1H-pyrazole.

20. A process according to claim 14 wherein Y represents a thiazolyl or oxazolyl moiety attached to the dihydropyrazole ring at one position adjacent to the oxygen or sulfur atom and possessing a substituent in the other position adjacent to the oxygen or sulfur atom.

21. A process according to claim 14 wherein Y represents 4,5-dihydro-3-(4-fluorophenyl)-4-(2-trifluoromethyl-5-thiazolyl)-1H-pyrazole, 4,5-dihydro-3-(4-fluorophenyl)-4-(3-trifluoromethyl-2-isothiazolyl)-1H-pyrazole, 4,5-dihydro-3-(4-fluorophenyl)-4-(2-trifluoromethyl-5-oxazolyl)-1H-pyrazole, or 3-(4-chlorophenyl)-4,5-dihydro-4-(2-trifluoromethyl-5-thiazolyl)-1H-pyrazole.

22. A process according to claim 14 wherein the N,N,N',N'-tetra(C$_1$-C$_3$)alkyldiaminomethane is N,N,N',N'-tetramethyldiaminomethane.

23. A process according to claim 14 wherein dichloromethane or chloroform is employed as the solvent.

24. A process according to claim 14 wherein trifluoroacetic acid is the acid or anhydride or is the catalytic strong acid.

25. A process according to claim 14 wherein acetic anhydride is the acid or anhydride and trifluoroacetic acid is the catalytic strong acid.

26. A process according to claim 14 wherein the temperature is maintained at about 0° C. to about 30° C. for the combination and about 10° C. to about 40° C. for the subsequent addition of hydrazine.

27. A process according to claim 14 wherein the product obtained is further, without isolation, treated with an isocyanate or isothiocyanate compound the formula $$Z-NCW$$

wherein

Z represents phenyl optionally substituted in the 4-position with F, Cl, Br, CN, COQ, R, OR', SR', SOR', SO$_2$R', OSO$_2$R', NO$_2$, or OAr and optionally in the 2-position with F and optionally in the 3- or 5-position with F, Cl, Br, CN, R, or OR'; and W represents O or S in an inert solvent to obtain a 3,4,N-triaryl-4,5-dihydro-1H-pyrazole-1-carboxamide compound of the formula wherein Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety wherein said substituents are selected from F, Cl, Br, CN, COQ, CF$_3$, OR', SR', NO$_2$, and OAr or a 5-membered aromatic heterocyclic ring moiety containing one ring oxygen or sulfur atom and one or two ring nitrogen atoms, which moiety is optionally substituted with one substituent selected from F, Cl, Br, CN, COQ, R, OR', SR', SOR', SO$_2$R', NO$_2$, and OAr and, in those moieties containing only one ring nitrogen atom, optionally additionally substituted with a F substituent;

X represents phenyl optionally substituted in the 4-position with F, Cl, Br, CN, COQ, R, OR', SR', SOR′, SO$_2$R′, NO$_2$, or OAr and/or in the 3-position with F, Cl, Br, CN, R, or OR′;

Z represents phenyl optionally substituted in the 4-position with F, Cl, Br, CN, COQ, R, OR′, SR′, SOR′, SO$_2$R′, OSO$_2$R′, NO$_2$, or OAr and optionally in the 2-position with F and optionally in the 3- or 5-position with F, Cl, Br, CN, R, or OR′;

W represents O or S;

R represents C$_1$–C$_3$ alkyl, C$_2$–C$_3$ alkenyl, or C$_2$–C$_3$ alkynyl optionally singly to completely substituted with fluorine or chlorine;

R′ represents C$_1$–C$_3$ alkyl optionally singly to completely substituted with fluorine or chlorine;

Ar represents phenyl optionally substituted with 1 or 2 compatible substituents selected from F, Cl, Br, CN, COQ, R, OR′, SR′, SOR′, SO$_2$R′, and NO$_2$; and Q represents OR″, SR″, NH$_2$, NHR″, or NR″$_2$.

* * * * *